United States Patent [19]

Bartrug et al.

[11] 4,073,849
[45] Feb. 14, 1978

[54] PROCESS FOR FORMING ELASTOMER FILMS

[75] Inventors: Norman G. Bartrug, Allison Park; Donald L. McDaniel, Lower Burrell, both of Pa.

[73] Assignee: PPG Industries, Inc., Pittsburgh, Pa.

[21] Appl. No.: 653,323

[22] Filed: Jan. 29, 1976

Related U.S. Application Data

[60] Division of Ser. No. 587,471, June 16, 1975, which is a continuation of Ser. No. 475,705, June 3, 1974, abandoned.

[51] Int. Cl.² .......................... B29H 8/00; B32B 25/04
[52] U.S. Cl. .................................. 264/236; 156/246; 260/845; 264/309; 264/320; 264/331; 427/196; 427/385 A; 427/422
[58] Field of Search ............... 264/299, 204, 309, 320, 264/331, 347, 236; 427/422, 385, 196; 260/845; 73/8, 95.5, 146, 150 R, 150 A; 156/242, 246

[56] References Cited

U.S. PATENT DOCUMENTS

| Re. 23,451 | 1/1952 | Mighton | 260/845 |
|---|---|---|---|
| 2,165,099 | 7/1939 | Hansen | 264/309 |
| 2,231,057 | 2/1941 | Dieterich | 264/320 |
| 2,439,157 | 4/1948 | Chavannes | 264/216 |
| 2,488,446 | 11/1949 | Swiss | 425/404 |
| 2,691,614 | 10/1954 | Wilson | 264/137 |
| 2,713,040 | 7/1955 | Brass et al. | 264/216 |
| 2,780,574 | 2/1957 | Ott et al. | 156/246 |
| 2,817,616 | 12/1957 | Wolfe | 264/137 |
| 2,822,311 | 2/1958 | Rowe et al. | 264/137 |
| 3,281,396 | 10/1966 | Barnes | 264/309 |
| 3,369,922 | 2/1968 | Svrchek | 427/318 |
| 3,619,252 | 11/1971 | Roscher | 427/318 |
| 3,655,353 | 4/1972 | Nalley et al. | 65/3 |

FOREIGN PATENT DOCUMENTS 761,423  11/1956  United Kingdom ................ 260/845

Primary Examiner—Jeffery R. Thurlow
Attorney, Agent, or Firm—John E. Curley

[57] ABSTRACT

A method of forming a continuous film of an elastomeric latex and a phenolic resin comprising spraying a plurality of coats of the aqueous admixture onto a nonadherent surface. The nonadherent surface is at a temperature of 120° F. or greater and each coat of the aqueous admixture is less than about 0.7 mil dry film thickness. The film so formed can be tested for physical properties and the testing results are capable of being correlated with the performance of glass fibers with the aqueous admixture coated thereon for reinforcement of elastomeric matrices.

2 Claims, No Drawings

PROCESS FOR FORMING ELASTOMER FILMS

REFERENCE TO CROSS-RELATED APPLICATIONS

This is a divisional of application Ser. No. 587,471, filed June 16, 1975, which is a continuation of application Ser. No. 475,705, filed June 3, 1974, now abandoned.

BACKGROUND OF THE INVENTION

This invention relates to a method of forming a continuous film from an aqueous admixture of an elastomeric latex and a phenolic resin.

It has long been recognized that glass fiber material makes an ideal reinforcement for rubber products such as automobile tires, power transmission belts and the like. In preparing glass fiber material for such applications, the individual glass fibers or groups of glass fibers in the form of strand, rope, cord, roving, fabric and the like are coated with a rubber adhesive to aid in bonding the glass to the elastomeric materials to be reinforced. The rubber adhesive generally comprises a resin and an elastomeric material to form a bond between the glass and the main body of material being reinforced.

Generally, in the production of fiber glass reinforcing cords or other bundle forms, individual fibers are coated with a sizing and then the fibers are brought together in bundle form. Commonly the sizing contains a coupling agent such as a silane, a lubricant or other ingredients to assist in the handling of the bundle during processing. The bundle is then coated by dipping or otherwise contacting it with a coating mixture containing an elastomeric latex and a homogeneous resinous component.

The term "elastomer" as used herein is intended to mean and include both synthetic and natural rubber. "Natural rubber" as used herein is the elastic solid obtained from the sap or latex of the Hevea tree, the major constituent being the homopolymer of 2-methyl 1,3-butadiene (isoprene). "Synthetic rubber" as used herein is meant to encompass polymers based upon at least 2 percent of a conjugated unsaturated monomer. The conjugation being in the 1,3 position in the monomer chain and the final monomer in its uncured state having an extensibility of at least 200 percent and a memory of at least 90 percent when stretched within the extensibility limits and released instantaneously. The conjugated unsaturated monomers which are used in the preparation of synthetic rubbers are, but not limited to, chloroprene, butadiene, isoprene, cyclopentadiene, dicyclopentadiene and the like. Other olefins capable of free radical anionic or cationic interpolymerization into the polymer chain with the conjugated unsaturated monomer are useful in forming synthetic rubbers. These olefins are typically monoethylenically unsaturated monomers. "Monoethylenically unsaturated" as used herein is characterized by the monomer having one $CH_2 = C<$ group. These monoethylenically unsaturated monomers are, but not limited to, the acrylic monomers such as methyacrylic acid, acrylic acid, acrylonitrile, methyacrylonitrile, methylacrylate, methylmethacrylate, ethylacrylate, ethylmethacrylate and the like. Monoolefinic hydrocarbons such as ethylene, butylene, propylene, styrene, alphamethylstyrene and the like and other functional mono unsaturated monomers such as vinyl pyridine, vinyl pyrrolidone and the like functional vinylic monomers.

Glass fibers are excellent reinforcing materials and are distinguishable from other fibrous reinforcing materials such as natural and synthetic organic fibers in that the glass fibers do not become elongated or deformed under stress to the extent that other fibers do. Unlike other fibers, particular combinations of glass fibers with encapsulating coatings cooperate to yield reinforcing materials that have greater tensile strength than either the glass or coating material alone. While other materials which are subject to substantial stress elongation are essentially limited in tensile strength to the basic strength of the bare fibers, even if coated, properly coated glass fibers have greater strength than the glass alone. For example, the low modulus of elasticity of glass may be exploited to provide reinforced tires having superior road performance if an appropriate coating medium is provided to transfer stresses to all fibers in the glass fiber cord so that loading throughout is substantially uniform. This phenomena is illustrated by the observation that a typical uncoated glass fiber cord [G-75, 5/0, filament count 2,000, i.e. 2,000 filament strands of G fibers, (about $3.7 \times 10^{-5}$ inches diameter), 7,500 yards per pound of glass] has a tensile strength of about 35 to 40 pounds by ASTM Test D578-52. This same cord when coated with an elastomer resorcinol-formaldehyde coating has a tensile strength of about 50 to 70 pounds.

A plurality of components are used in the coating composition for the glass fibers to impart various properties thereto. Among these components are elastomers, as previously described, and phenolic resins especially resorcinol-formaldehyde resins. Further, carboxylated polymers are sometimes added to the dip material to impart adhesion and improve tensile strength. Waxes are sometimes added to the dip formulation to provide stability to ultraviolet light. Due to the plurality of components used in coating compositions which determine the final properties of the cord, a great deal of formulation must be conducted in order to find an acceptable or improved coating composition for the glass fiber cord.

Because there are so many components and the extent of the interaction of the ratios and compositions of these components is not completely known, physical testing of the tire cord is necessary in order to determine if a product is acceptable for final use.

Testing methods of the cord are conducted both in the laboratory and in the field. Laboratory testing is composed of both the testing of the cord itself and the testing of the cord embedded in a rubber matrix. The normal testing of the cord itself is usually by a tensile strength measurement. When the cord is embedded in a rubber matrix the composite is tested for its flexibility in accordance with the Scott flex test. The Scott flex test involves taking strips of rubber cord composite and flexing this composite for the desired number of cycles. After the cycles have been completed, the composite is inspected for breakage of glass filaments. This test is used as an indication of how the glass fiber cord will perform in its final use, i.e., tires, or power transmission belts.

In testing the adhesion of the cord to a rubber matrix the cord is embedded in the rubber matrix and sectioned so that the interface of the cord and the rubber matrix can be pulled in opposite directions in an Instron ® testing device. This test for adhesion is also considered to be indicative of how the cord will perform in its final application.

Although these laboratory tests have been found to be somewhat representative of the quality of the glass fiber cord, these testing methods are not always reliable in predicting the final performance of the glass fiber cord. Therefore, field testing of the cord in tires and in power transmission belts must be made.

In order to field test the cord, it must be used in the construction of a tire. Therefore, individual tires having the cords to be tested are fabricated and run through various destructive testing techniques such as riding a car with the tires to be tested over a course of cobblestones for a certain number of miles; running the tires to be tested at high speed and low speed and finally after the predetermined amount of driving time has been completed, the tires are X-rayed and inspected for broken filaments in the cord.

The laboratory testing techniques do not involve great expense in both time and materials; however, the field testing of the tires which is the true indication of the performance of the cord amounts to a great deal of cost due to the expense in building the tires and testing the tires. It has been hypothesized by workers in this area that if the physical properties of the glass fiber coating formulation could be determined, an indication of the final properties of the tires could be obtained. However, the continuous, uniform, free films of the coating composition have not heretofore been able to be produced. This is attributable to the fact that when the coating composition as such is coated on a substrate, in a film thickness acceptable for testing, on drying the film cracks and becomes discontinuous or forms a powder; therefore, losing all utility for any type of testing technique.

The instant invention provides a method of forming a uniform continuous, free film of adequate thickness to test the physical characteristics of the elastomeric latex - phenolic resin admixture in its cured state.

SUMMARY OF THE INVENTION

A process for forming a continuous film from an aqueous admixture of an elastomeric latex and a phenolic resin comprises spraying the admixture onto a surface being heated to a temperature of greater than 120° F. A sufficient amount of the admixture is sprayed onto the surface to form a base coat film of less than about 0.7 mil. Subsequent coats of the admixture are sprayed onto the base coat to impart a coating thickness of less than 0.7 mil per coat to form a uniform final film of greater than about 4 mils. The heated surface is composed of a nonadhesive material such as Teflon ® fluorocarbon or the like so that the film can be easily removed from the heated surface.

As previously discussed, a broad range of elastomeric latices have been used to form the strands, yarns and cords which are characterized as glass fiber bundles. Particular elastomeric latices suited for use in this invention include styrene-butadiene-vinylpyridine terpolymers, neoprene, polyisoprene, butyl rubber, butadiene-styrene copolymers (styrene-butadiene-rubber) acrylonitrile-butadiene-vinylpyridine terpolymers and the like.

Useful resins employed in this invention include resorcinolformaldehyde resins, phenol-formaldehyde resins and the like. Both the resole and novolac type phenolic aldehyde resins have been found to be useful in forming the rubber adhesive coating composition. The resole resins are characterized by the formation of the resin induced by base catalysis and the novolac resins are characterized by their formation by acid catalysis. Generally, the resole resins are more highly methylolated than the novolacs. The choice between the resole or nonvolac resin in the rubber adhesive coating composition is contingent on the other materials used in the coating composition itself and the desired properties of the final glass fiber bundle. Rubber adhesive systems which are useful in the practice of the invention include those disclosed in U.S. Pat. Nos. 2,691,614; 2,817,616 and 2,822,311 which are incorporated herein by reference and made a part hereof.

Other materials may be included in the coating composition which impart the desired properties to the final coated cord. These materials are typically silicone coupling agents, waxes and like additives.

Typical silicone coupling agents are, but not limited to, the amino silane coupling agents, such as gamma-aminopropyltriethoxysilane, N-beta aminoethyl gamma-aminopropyltrimethoxysilane and the like. Other functional silanes may also be utilized such as vinyl beta-methoxyethoxysilane, gamma-glycidoxypropyltrimethoxysilane, vinyltriacetoxysilane and the like.

In the principle of the invention, the heated substrate has a temperature greater than 120° F. so that the volatile components of the coating composition are substantially removed from the coating composition as they are coated on the substrate. In order that substantially all of the volatiles are removed, the base film is preferably less than about 0.7 mil to aid in evaporation of the volatiles. If the final film thickness of a single coat is greater than 0.7 mil, cracking and discontinuity of the film will occur and its utility as a testing specimen will be impaired if not completely destroyed.

The final film immediately before removal from the heated substrate is substantially water free. "Substantially water free" as used herein means that the film contains less than 5 percent by weight water and is greater than 94 percent by weight solid content.

It is preferred that the temperature of the heated surface be below the temperature of curing of the coating composition. This allows the curing of the film to be conducted at a separate stage and under processing conditions which will more adequately approximate the curing of the coated cord during commercial processing.

It has been determined that representative film thicknesses of 4 mils or greater are necessary to adequately predict the final properties of a particular coating composition on the glass fiber cord, and more preferably, final film thicknesses of 4 to 23 mils most closely approximate the performance of the cord in their final use.

The invention will be further elucidated by the following embodiments.

DESCRIPTION OF PREFERRED EMBODIMENTS

The coating admixtures useful in forming the films of the invention have the following typical composition:

| Ingredient | Range in Parts By Weight |
|---|---|
| Elastomeric latex, 40 – 60 percent solids in water | 150 – 380 |
| Water | 60 – 110 |
| NH$_4$OH | 0.2 – 1 |
| Phenolic resin, 50 – 90 percent solids in water | 6 – 28 |
| Formaldehyde (37 percent) | 2.5 – 14.5 |
| Water | 1.0 – 8.0 |

| Ingredient | Range in Parts By Weight |
|---|---|
| Wax | 0 – 52 |

Preferred total solids content of about 28 – 33 percent by weight.

The admixtures are prepared by adding the larger volume of water to an agitating premix tank followed by the addition of ammonium hydroxide. The phenolic resin is added to this mixture with containing stirring until complete dissolution of the resin occurs. The elastomeric latex is added to a batch tank and to it is added the contents of the premix tank with stirring which is continued for about five minutes after the addition of the premix. The formaldehyde is added to the mixture and the mixture is stirred for about ten minutes. A solution of the wax is added with agitation. This coating mixture is allowed to age for at least two hours before use.

The wax component of the formulation is typically a microcrystalline wax or a paraffin wax. The microcrystalline wax has a melting point of at least 100° C. and preferably 135° C. The paraffin wax has a preferred melting range of 50° C. to 90° C. Other waxes known to those skilled in the art may be utilized in forming the coating compositions of the invention.

A Teflon ® fluorocarbon (manufactured by du Pont) coated steel hot plate cover is placed over a variable temperature hot plate which is preheated so that the temperature of the Teflon ® floropolymer surface is greater than 120° F. but below the curing temperature of the coating composition. The edges of the hot plate cover are masked using masking tape with an underlying disposable protective surface to prevent overspray onto the hot plate other than the Teflon ® fluorocarbon coated area. An air pressurized spray gun is utilized in spraying the coating composition. It has been found that a spraying pressure of about 40 pounds per square inch with a setting on the spray gun for a fine spray, forms an excellent film.

A uniform base coat of the coating composition covering the hot plate cover is considered as one pass, with each subsequent pass adding thickness to the film. The path of the gun on each pass is at 90° to that of the preceding pass, thereby eliminating the possibility of nonuniformity of film thickness which occurs by subsequent coats being applied at the same direction as the previous coats. The thickness of the sample or the final dry coating composition depends upon the percent solids of the dip and the setting of the gun. Typically, nine passes with the spray gun across the hot plate cover will produce a 5 mil dry film and 40 passes with the spray gun across the hot plate cover will produce a film of about 20 mils when the spray gun is set for fine spray and the coating composition is at about 27 to 35 percent by weight solids.

After the last coat of the coating composition is applied to the substrate, the film is stripped from the Teflon ® fluorocarbon coated hot plate after substantially all of the water is removed therefrom and placed in a heated press at or above the curing temperature of the coating compositions solids, approximately 300° F. A curing time of 1 to 2 minutes and a pressure of 1,000 pounds per square inch is adequate to cure the coating composition solids. The film is removed from the press and is ready for testing after cooling to room temperature.

EXAMPLE I

A Teflon ® fluorocarbon coated, steel hot plate cover is placed over a Lindburg variable temperature hot plate. The hot plate is preheated so that the temperature of the Teflon ® fluorocarbon surface is about 120° F. The edges of the cover are masked using masking tape with an underlying disposable protective surface to prevent overspray onto the hot plate other than the Teflon ® fluorocarbon coated area.

A Binks Model 18, one quart spray gun is utilized in spraying the coating composition. The air pressure utilized in spraying is 40 pounds per square inch and the setting on the spray gun is for a fine spray. A coating composition having the following ingredients is charged to the reserve tank of the spray gun:

| Ingredient | Parts by Weight |
|---|---|
| Gentac ® Latex 121 (Styrene: butadiene: vinylpyridine, 15.5:73.5:11, 41 percent solids in water) | 244 |
| Water | 89 |
| Penacolite ® Resin (resorcinol-formaldehyde novolac resin, 0.6 formaldehyde: 1 resorcinol, 70 percent solids in water) | 15.7 |
| Ammonia (28 percent in water) | 0.5 |
| Formalin (37 percent formaldehyde) | 6.75 |
| Water | 4.0 |
| Mobilcer ® Q wax (microcrystalline wax 50 percent solids in water) | 10 |
| 32 percent solids content | |

A uniform base coat of coating covering the entire hot plate was considered as one pass being sprayed on the hot plate cover with each subsequent pass adding thickness to the sample. The course of the gun on each pass is at 90° to that of the preceding pass thereby eliminating the possibility of nonuniformity of film thickness which occurs by subsequent coats being applied at the same direction as previous coats. Nine coats of substantially equal thickness of the coating admixture were sprayed onto the hot plate cover.

After coating, the film was allowed to dry until tack free on the hot plate cover. After drying the sample film was stripped from the hot plate cover. The free film was smooth and continuous. The film was placed in a mold and cured at 1000 pounds per square inch for 1 minute.

Three samples as produced above were made which had an average film thickness of 4 to 7 mils.

EXAMPLES II – V

Four coating admixtures were prepared in accordance with Example I except that the amount of Penacolite ® resin was varied. The following table represents the variation of phenolic resin in these examples:

| Example | Phenolic Resin (Penacolite ® Resin) Level |
|---|---|
| II | 11.4 parts |
| III | 19.8 parts |
| IV | 24.2 parts |
| V | 28.6 parts |

Films of each of the admixtures were produced in accordance with the procedure of Example I and tested for tensile strength, percent elongation and 10 percent modulus.

Tensile strengths of the films were tested as follows. Three samples were cut from each of the films of Examples I through V. The samples had the dimensions of 4 inches by 0.25 inch and a thickness between 4 and 7 mils. One end of the sample was placed in one jaw of an Instron ® test device while the opposite end was placed in another jaw of the test device. The test span was 1.25 inches with a pull rate of two inches per minute. The jaws of the test instrument were traveled in opposite directions until the sample separated. At the point of separation, the force required to obtain separation was recorded. Three samples of each film of Examples I through V was tested. The tensile strengths as obtained above for each example were averaged. The average tensile strength of the films of the examples is recorded on Table 1.

Percent elongation was run by the same method as tensile strength, only at the point of sample separation the distance between the Instron ® jaws was recorded. From this value was substracted the original length of the sample, and percent elongation was calculated. The average percent elongation for the films of each example are reported in Table 1.

Ten percent modulus was run by the same method as both tensile strength and elongation except that the samples were elongated 10 percent of their original length and the force required to elongate the samples was recorded.

Table 1

| Example | Dip Composition Parts Resin | Tensile P.S.I. | Percent Elongation | 10 Percent Modulus P.S.I. |
|---------|-----------------------------|----------------|--------------------|---------------------------|
| I       | 11                          | 1269           | 26.5               | 1033                      |
| II      | 8                           | 790            | 29.12              | 627                       |
| III     | 14                          | 1456           | 19.6               | 1334                      |
| IV      | 17                          | 1865           | 12.2               | 1877                      |
| V       | 20                          | 2186           | 11.0               | 2085                      |

EXAMPLES VI - X

Samples of glass fiber cord, G-75, 5/0 were sized with the following composition:

| Ingredient | Amount |
|------------|--------|
| Versamide 140 (polyamino polyamide condensation product of dimer acid and a polyamine) | 26.9 pounds |
| Abraze-Ade (non-ionic emulsion of 12 percent polypropylene, 12 percent polyethylene and 6 percent emulsion-stabilizer) | 389.8 pounds |
| Alamine 7D (stearyl amine, cationic surface active agent) | 2.7 pounds |
| Nalco D-2226 (acetate salt of the condensation product of aminoethylethanoamine and hydrogenated tallow fat. | 8.2 pounds |
| A-1100 (gamma-aminopropyltriethoxysilane) | 15.3 pounds |
| Sag 470 (silicone anti-foam agent) | 120 milliliters |
| Acetic acid | 3300 milliliters |
| Sufficient water to make 300 gallons | |

The glass fibers were sized in accordance with the method described in U.S. Pat. No. 3,655,353, incorporated herein by reference and were coated with the compositions of Examples I through V. The coating method was in accordance with the method described in U.S. Pat. No. 3,619,252, incorporated herein by reference.

According to the method of U.S. Pat. No. 3,619,252 a plurality of glass fiber strands each having a slight twist to provide strand integrity which have been previously sized are combined in parallel relation and passed through a guide in tangential contact across motor driven rollers. The rollers are partially immersed in one of the coating compositions of Examples I through V and these rollers pick up this coating composition when rotated. The coating which is picked up is brought into contact with the glass fiber strands, coating and impregnating the combined bundle of strands. Relaxation of tension in the combined bundle of strands opens the spacing between the fibers and between the strands enhancing impregnation of the coating composition into the bundle. The total impregnation is limited by the volume available between the fibers and strands and by the volume of coating solids in the total dip volume which fills the voids in the bundle. High solids concentration in the dip is utilized when it is desired to obtain full impregnation with the coating composition and not merely with water. The coating composition solids were applied in order that the cords so formed would be composed of 30 percent of the dried coating composition based on dry glass weight.

After coating the fiber glass bundle with a coating composition for sufficient time to fully impregnate the bundle with the water and solids containing composition, the bundle is passed through a dielectric heater or drying oven. The drying oven is so designed and operated that water is removed rapidly from inside the bundle as well as from the surface of the bundle without substantial migration of the solids from the interior to the surface of the bundle and without excessive blistering.

The dried glass fiber bundle is then subjected to heat to partially cure the rubber adhesive coating throughout the bundle. It is preferable to partially cure the coating while the coated fiber remains separate and to complete the curing of the coating on the glass fiber bundle when it is embedded in the rubber being reinforced during the curing of the rubber in the final article.

Five series of glass fiber cord were made, each having the sizing composition previously described and each set having a different coating composition, those being of Examples I through V.

From these glass fiber cords, five series of tires were made and tested by mounting the tires on an automobile and running the automobile over a cobblestone test track. Periodically the test was interrupted and the tires were X-rayed to determine the breakage of the individual filaments in the tire cord. The following table represents the performance of the cords coated with compositions of Examples I through V:

Table 2

| Example | Laps Per First 50 Breaks |
|---------|--------------------------|
| I       | 480                      |
| II      | 120                      |
| III     | 2160                     |
| IV      | 4920                     |
| V       | 8400                     |

Thus it can be seen from the combined data of Table 1 and 2 that the quantitative improvement in the performance of cord in a reinforced article is proportional to various properties of a free film of the coating composition. This improvement is generally inversely proportional to the tensile strength of the film, directly proportional to the elongation of the film and inversely proportional to the 10 percent modulus of the film. Therefore the films of the instant invention provide a means for economical testing of glass fiber coating compositions to correlate with how glass fibers with these coating compositions will perform in reinforced elastomeric articles.

While the present invention has been described with reference to particular perferred embodiments, it will be appreciated by those skilled in the art that variations may be employed without departing from the spirit of the invention and the invention is only to be limited insofar as set forth in the accompanying claims.

We claim:

1. A method of forming a continuous film from an aqueous admixture comprising an elastomeric latex and a phenolic resin, comprising:

spraying an amount of said admixture onto a surface to form a coat thereon, said surface being maintained at a temperature greater than 120° F., the amount of sid admixture sprayed thereon being sufficient to form a base film coat of less than about 0.7 mil thickness, and the adhesion between said surface and said film being less than the cohesion within said film, and spraying a plurality of additional coats of said admixture over said base film, each of said additional coats being regulated in the amount sprayed to impart a coat thickness of each coat of less than about 0.7 mil to thereby form a continuous, uniform final film having a thickness greater than 4 mils, removing said final film from said substrate, drying said film to remove substantially all water therefrom and then subjecting said final film to heat at sufficient pressure to cure said film.

2. The method of claim 1, wherein each coat is plied at an angle of 90° to that of the preceding coat.

* * * * *